United States Patent [19]

Turner

[11] Patent Number: 4,877,773

[45] Date of Patent: Oct. 31, 1989

[54] PHARMACEUTICAL PREPARATION

[76] Inventor: Leola E. B. Turner, Main St., Greensboro, Ga. 30642

[21] Appl. No.: 43,761

[22] Filed: Apr. 29, 1987

[51] Int. Cl.$^4$ .................... A61K 33/04; A61K 31/715
[52] U.S. Cl. ...................... 514/23; 514/892; 424/713
[58] Field of Search .................. 424/164; 514/23, 892

[56] References Cited

U.S. PATENT DOCUMENTS

| Number | Date | Inventor | Class |
|---|---|---|---|
| 295,078 | 3/1884 | Thatcher | 424/164 |
| 1,621,131 | 3/1927 | Nelson | 424/164 |
| 1,759,182 | 5/1930 | Bender et al. | 514/892 |
| 1,987,005 | 1/1935 | Forbes | 424/164 |
| 2,367,166 | 1/1945 | Balston | 514/892 |
| 3,826,827 | 7/1974 | Forest et al. | 424/164 |
| 4,225,587 | 9/1980 | Hess | 424/164 |
| 4,405,604 | 9/1983 | Sunley | 424/162 |
| 4,476,121 | 10/1984 | Moss | 424/195.1 |
| 4,613,498 | 9/1986 | Crosby | 514/882 |
| 4,616,039 | 10/1986 | Herschler | 514/711 |
| 4,626,287 | 12/1986 | Shah et al. | 514/892 |

FOREIGN PATENT DOCUMENTS 60-36416 2/1985 Japan .

Primary Examiner—Ronald W. Griffin

[57] ABSTRACT

The present invention relate to compositions comprising ½ equal part epsom salt, 1 equal part molases syrup, 1 equal part castor oil and ½ equal part amorphous sulfur.

2 Claims, No Drawings

PHARMACEUTICAL PREPARATION

COMPOSITION (Description)

A. Epsom salts—consist of hydrated magnesium sulfate.

B. Molasse syrup—consist of 65% carbohydrates, 24% water, 6% protein, 5% ash.

C. Castor oil—consist of glycerol (a type of alcohol), fatty acids (vegetable oil-non edible).

D. Sulfur—amorphous (yellowish).

THE PROCESS EMBODIMENT (Compound matters)

½ equal part epsom salts; 1 equal part molasse syrup; 1 equal part castor oil; ½ equal part sulfur.

THE MODE OF OPERATION

One (1) tablespoon full before breakfast for nine (9) consecutive mornings.

This composition improves the purification of the circulatory system and improves the elimination process of the endocrine system.

I claim:

1. A composition comprising ½ equal part epson salt, 1 equal part molasses syrup, 1 equal part castor oil and ½ equal part amorphous sulfur.

2. A pharmaceutical preparation comprising the composition of claim 1.

* * * * *